US010966955B2

(12) United States Patent
Lai et al.

(10) Patent No.: US 10,966,955 B2
(45) Date of Patent: Apr. 6, 2021

(54) OCULAR DRUG DELIVERY SYSTEM AND USES THEREOF

(71) Applicant: Chang Gung University, Taoyuan (TW)

(72) Inventors: Jui-Yang Lai, Taoyuan (TW); Li-Jyuan Luo, Taoyuan (TW); Chung-Cheng Lo, Taoyuan (TW); Duc Dung Nguyen, Taoyuan (TW)

(73) Assignee: Chang Gung University, Taoyuan (TW)

( * ) Notice: Subject to any disclaimer, the term of this patent is extended or adjusted under 35 U.S.C. 154(b) by 0 days.

(21) Appl. No.: 16/818,078

(22) Filed: Mar. 13, 2020

(65) Prior Publication Data

US 2021/0059980 A1 Mar. 4, 2021

(51) Int. Cl.

| | |
|---|---|
| *A61K 9/127* | (2006.01) |
| *A61K 9/06* | (2006.01) |
| *A61K 45/06* | (2006.01) |
| *A61K 47/36* | (2006.01) |
| *A61K 31/353* | (2006.01) |
| *A61P 27/02* | (2006.01) |
| *A61K 9/00* | (2006.01) |

(52) U.S. Cl.
CPC .......... *A61K 31/353* (2013.01); *A61K 9/0048* (2013.01); *A61K 9/06* (2013.01); *A61K 9/127* (2013.01); *A61K 45/06* (2013.01); *A61K 47/36* (2013.01); *A61P 27/02* (2018.01)

(58) Field of Classification Search
CPC ........ A61K 31/353; A61K 9/06; A61K 45/06; A61K 9/127; A61K 9/0048; A61K 47/36; A61P 27/02
See application file for complete search history.

(56) References Cited

U.S. PATENT DOCUMENTS

| | | | |
|---|---|---|---|
| 8,399,025 B2* | 3/2013 | Roy | A61K 47/61 424/501 |
| 2014/0199376 A1* | 7/2014 | Mousa | A61K 31/192 424/450 |
| 2016/0184222 A1* | 6/2016 | Gaillard | A61K 9/127 424/429 |
| 2019/0151243 A1* | 5/2019 | Barenholz | A61K 9/127 |
| 2020/0222559 A1* | 7/2020 | Elangovan | A61K 31/712 |
| 2020/0297856 A1* | 9/2020 | Payne | C08J 3/075 |

FOREIGN PATENT DOCUMENTS

WO 2014/039012 * 3/2014

OTHER PUBLICATIONS

Li, N et al in Drug Dlievery, vol. 19, # 1, pp. 28-35, 2011.*

* cited by examiner

*Primary Examiner* — Gollamudi S Kishore
(74) *Attorney, Agent, or Firm* — Cesari & McKenna, LLP

(57) ABSTRACT

Disclosed herein is an ocular drug delivery system, comprising a positively charged chitosan-modified hydrogel, a secretory phospholipase A2 (sPLA2) hydrolysable liposome encapsulating an anti-inflammatory drug and having a negative surface charge, a first thiolated hyaluronic acid (HA-SH) nanoparticle encapsulating a wound-healing drug and having a negative surface charge, and a second HA-SH nanoparticle encapsulating a transforming growth factor-β inhibitor and having a negative surface charge. The sPLA2 hydrolysable liposome and the first and second HA-SH nanoparticles are attached to the positively charged chitosan-modified hydrogel by electrostatic attraction. Uses of the system are also disclosed.

19 Claims, 4 Drawing Sheets

Specification includes a Sequence Listing.

| Slit-lamp | Normal control group | Negative control group | Positive control group | Experimental group 1 | Experimental group 2 |
|---|---|---|---|---|---|
| 2 hours | | | | | |
| 1 week | | | | | |
| Fluorescein staining | Normal control group | Negative control group | Positive control group | Experimental group 1 | Experimental group 2 |
| 2 hours | | | | | |
| 1 week | | | | | |

FIG. 7

OCULAR DRUG DELIVERY SYSTEM AND USES THEREOF

CROSS-REFERENCE TO RELATED APPLICATION

This application claims priority of Taiwanese Patent Application No. 108130400, filed on Aug. 26, 2019.

FIELD

The present disclosure relates to an ocular drug delivery system and a method for treating an ocular disorder.

BACKGROUND

Diseases affecting the cornea are a major cause of blindness worldwide, second only to cataract in overall importance. The epidemiology of corneal blindness is complicated and encompasses a wide variety of infectious and inflammatory eye diseases that cause corneal scarring, which ultimately leads to functional blindness. The corneal epithelium is composed of two to three cell layers of flattened superficial cells, two to three cell layers of wing cells, and a single layer of columnar basal cells. The superficial cells adhere to one another via desmosomes, and such cells are encircled by tight junctions. Due to these tight junctions, the corneal epithelium represents the rate-limiting barrier for the permeation of therapeutic drugs. Therefore, the development of strategies to overcome these barriers for the targeted ocular delivery of drugs, e.g. to the cornea, remains a major challenge.

Because of the presence of natural phospholipids, cell-like membrane and excellent biocompatibility, liposomes are a promising means of delivering ocular drugs. When applied topically, liposomes can attach to the hydrophobic corneal epithelium, where they continuously release the bound drug content, improving pharmacokinetics and decreasing toxic side effects. Studies have shown that liposomes can be prepared and are hydrolysable by secretory phospholipase A2 (sPLA2) and that hydrolysis by sPLA2 leads to release of the drug encapsulated within the liposome. Moreover, the products of sPLA2 hydrolysis, a lysolipid and a fatty acid act as permeabilizers of cell membranes leading to increased cell uptake of the drug. Since sPLA2 levels are elevated in cancerous tissues and at sites of inflammation (e.g., dry eye disease, chronic blepharitis, chronic ocular surface inflammation, and contact lens intolerance), sPLA2 activated liposomes may be used to preferentially deliver encapsulated drugs to such sites.

It is well known that hyaluronic acid (HA), a naturally-occurring glycosaminoglycan (GAG), plays a key role in wound healing. The structure of HA consists of repeating disaccharide units of D-glucuronic acid and N-acetyl-D-glucosamine linked by β-1-3 and β-1-4 glycosidic bonds. Purified native HA has many biomedical applications, including viscosurgery, viscosupplementation and wound healing.

Hydrogels are formed by crosslinked polymers and are able to absorb high quantity of water without being dissolved. HA hydrogels are physically or covalently cross-linked HA gels. HA molecules are generally functionalized to allow reaction with a cross linker. Crosslinked HA hydrogels, for example, can be prepared by crosslinking with molecules such as diepoxybutane, ethylene glycol diglycidyl ether (EGDGE) or polyethylene glycol diglycidyl ether (PEGDE).

HA hydrogels have been used for several applications including drug delivery applications, and they are able to provide sustained, local delivery of a variety of therapeutic agents. Use of HA as a scaffold material in hydrogels has been pursued due to the biocompatibility, low toxicity, lack of immune response and biodegradability of HA hydrogels. Although HA hydrogels have been studied for drug delivery applications, the delivery rates are difficult to control. If a hydrophilic drug is incorporated into a hydrogel, the incorporation is easy (large amounts can be loaded), but drug release is also rapid. On the other hand, it is difficult to get large amounts of hydrophobic drugs into such hydrogels, for solubility reasons. Any un-dissolved drug will migrate to the surface of a hydrogel and be released in a burst (within a day or two).

Thiolated polymers or so-called thiomers have recently gained considerable attention as platforms for controlled drug delivery. Thiomers might be useful to overcome the oral bioavailability problems associated with various categories of therapeutic agents such as peptides, antisense oligonucleotides, heparins or cephalosporines. Mucoadhesive matrix tablets, patches or microparticles are useful for, intraoral, peroral and ocular, local or systemic delivery. Another purpose of thiol modification is to combine the mucoadhesive features of hyaluronic acid with the new thiomer technology for the improvement of mucoadhesion (Kafedjiiski K. et al. (2007), *International Journal of Pharmaceutics*, 343:48-58).

In spite of the aforesaid, there is still a need to develop a new ocular drug delivery system that can repair damaged corneal tissues and exhibit satisfactory efficacy in treating ocular diseases.

SUMMARY

Accordingly, in a first aspect, the present disclosure provides an ocular drug delivery system, comprising:

a positively charged chitosan-modified hydrogel which is obtained by a process including subjecting a hydrogel to a click chemistry reaction with a chitosan;

a secretory phospholipase A2 (sPLA2) hydrolysable liposome encapsulating an anti-inflammatory drug and having a negative surface charge;

a first thiolated hyaluronic acid (HA-SH) nanoparticle encapsulating a wound-healing drug and having a negative surface charge; and a second HA-SH nanoparticle encapsulating a transforming growth factor-β (TGF-β) inhibitor and having a negative surface charge, the second HA-SH nanoparticle having a higher degree of crosslinking than that of the first HA-SH nanoparticle;

wherein the sPLA2 hydrolysable liposome, the first HA-SH nanoparticle, and the second HA-SH nanoparticle are attached to the positively charged chitosan-modified hydrogel by electrostatic attraction.

In a second aspect, the present disclosure provides a method for treating an ocular disorder in a subject, which includes administering to an eye of the subject an ocular drug delivery system as described above.

BRIEF DESCRIPTION OF THE DRAWINGS

The above and other objects, features and advantages of the present disclosure will become apparent with reference to the following detailed description and the exemplary embodiments taken in conjunction with the accompanying drawings, in which:

FIG. 7 shows the slit-lamp biomicroscopic images of rabbit eyes at 2 hours and 7 days after instilling fluorescein sodium.

DETAILED DESCRIPTION

Figure 1:
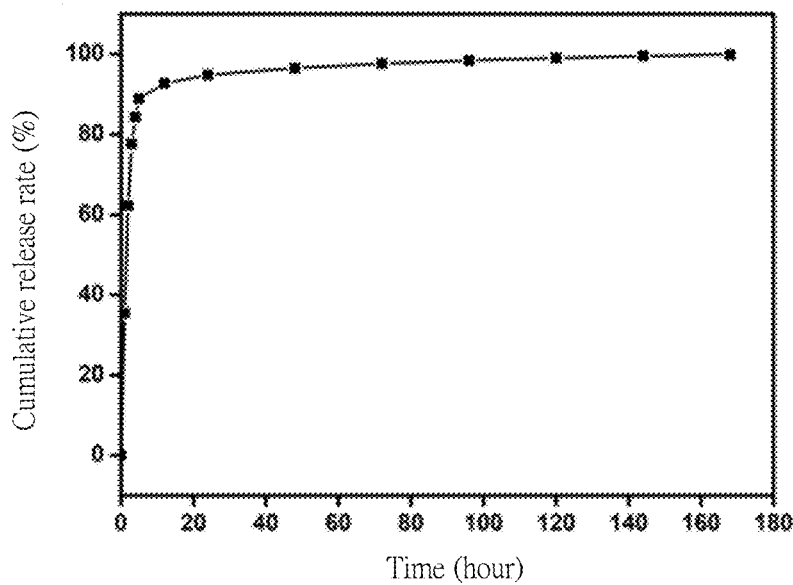
FIG. 1 shows the cumulative release profile of epigallocatechin gallate.

It is to be understood that, if any prior art publication is referred to herein, such reference does not constitute an admission that the publication forms a part of the common general knowledge in the art, in Taiwan or any other country.

For the purpose of this specification, it will be clearly understood that the word "comprising" means "including but not limited to", and that the word "comprises" has a corresponding meaning.

Unless defined otherwise, all technical and scientific terms used herein have the meaning commonly understood by a person skilled in the art to which the present disclosure belongs. One skilled in the art will recognize many methods and materials similar or equivalent to those described herein, which could be used in the practice of the present disclosure. Indeed, the present disclosure is in no way limited to the methods and materials described.

The present disclosure provides an ocular drug delivery system, comprising:

a positively charged chitosan-modified hydrogel which is obtained by a process including subjecting a hydrogel to a click chemistry reaction with a chitosan;

a secretory phospholipase A2 (sPLA2) hydrolysable liposome encapsulating an anti-inflammatory drug and having a negative surface charge;

a first thiolated hyaluronic acid (HA-SH) nanoparticle encapsulating a wound-healing drug and having a negative surface charge; and a second HA-SH nanoparticle encapsulating a transforming growth factor-β (TGF-β) inhibitor and having a negative surface charge, the second HA-SH nanoparticle having a higher degree of crosslinking than that of the first HA-SH nanoparticle;

wherein the sPLA2 hydrolysable liposome, the first HA-SH nanoparticle, and the second HA-SH nanoparticle are attached to the positively charged chitosan-modified hydrogel by electrostatic attraction.

As used herein, the term "click chemistry" refers to a collection of reactive members having a high chemical potential energy capable of producing highly selective, high yield reactions. The reactive members react to form extremely reliable molecular connections in most solvents, including physiologic fluids, and often do not interfere with other reagents and reactions. Examples of click chemistry reactions include Huisgen cycloaddition, Diels-Alder reactions, thiol-alkene reactions, and maleimide-thiol reactions. These reactions represent highly specific reactant pairs that have a chemoselective nature, meaning that they mainly react with each other and not other functional groups.

According to the present disclosure, the click chemistry reaction may be performed using a chemical agent selected from the group consisting of azidated epichlorohydrin, sodium azide, sodium nitrite, triflyl azide, imidazole-1-sulfonyl azide hydrochloride, and a combination thereof. In an exemplary embodiment, the chemical agent is sodium azide.

According to the present disclosure, the positively charged chitosan-modified hydrogel may have a UV-blocking material selected from the group consisting of ZnO, $TiO_2$, $CeO_2$, and a combination thereof. In an exemplary embodiment, the UV-blocking material is ZnO.

As used herein, the term "sPLA2 hydrolysable liposome" refers to a liposome that is hydrolysable by sPLA2 under physiological conditions (such as in cancerous tissues or at sites of inflammation). Such hydrolysis by sPLA2 leads to release of the drug encapsulated within the liposome.

According to the present disclosure, the sPLA2 hydrolysable liposome may have a phospholipid selected from the group consisting of dipalmitoyl-phosphatidylcholine (DPPC), anionic dipalmitoyl-phosphatidylglycerol (DPPG), and a combination thereof. In an exemplary embodiment, the phospholipid is dipalmitoyl-phosphatidylcholine.

According to the present disclosure, the anti-inflammatory drug may be selected from the group consisting of a phenolic drug, a flavonoid drug, an antibiotic, a steroid drug, a non-steroidal anti-inflammatory drug, and a combination thereof.

According to the present disclosure, the phenolic drug may be selected from the group consisting of epigallocatechin gallate (EGCG), p-coumaric acid, ferulic acid, gallic acid, gentisic acid, 4-hydroxybenzoic acid, protocatechuic acid, sinapinic acid, syringic acid, vanillic acid, and a combination thereof.

According to the present disclosure, the flavonoid drug may be selected from the group consisting of (+)-catechin, (+)-gallocatechin, (−)-epicatechin (EC), (−)-epigallocatechin (EGC), and a combination thereof.

According to the present disclosure, the antibiotic may be selected from the group consisting of tobramycin, besifloxacin, ciprofloxacin, levofloxacin, ofloxacin, levofloxacin, moxifloxacin, and a combination thereof.

According to the present disclosure, the steroid drug may be selected from the group consisting of dexamethasone, hypromellose, betamethasone sodium phosphate, prednisolone acetate, prednisolone sodium, and a combination thereof.

According to the present disclosure, the non-steroidal anti-inflammatory drug may be selected from the group consisting of ketorolac, bromfenac, diclofenac, flurbiprofen, nepafenac, phenylephrine, and a combination thereof.

According to the present disclosure, the preparation processes of the first HA-SH nanoparticle and the second HA-SH nanoparticle are within the expertise and routine skills of those skilled in the art (for example, see Kafedjiiski K. et al. (2007), *International journal of pharmaceutics*, 343(1-2), 48-58; Laffleur F. et al. (2014), *Journal of pharmaceutical sciences*, 103(8), 2414-2423; and Lee G. Y. et al. (2015), *Biomaterials*, 53, 341-348).

According to the present disclosure, the first HA-SH nanoparticle may have a crosslinking index ranging from 0% to 25%. In an exemplary embodiment, the first HA-SH nanoparticle has a crosslinking index of 19%.

According to the present disclosure, the second HA-SH nanoparticle may have a crosslinking index ranging from 26% to 50%. In an exemplary embodiment, the second HA-SH nanoparticle has a crosslinking index of 42%.

According to the present disclosure, the wound-healing drug may be selected from the group consisting of β-1,3-glucan, human growth hormone (HGH), insulin-like growth factor 1 (IGF-1), insulin, testosterone, and a combination thereof.

According to the present disclosure, the TGF-β inhibitor may be selected from the group consisting of trabedersen, TGF-β receptor type I antisense oligonucleotide AP-11014, lerdelimumab, metelimumab, fresolimumab GC-1008, D10 monoclonal antibody, TGF-β receptor type 1/type II inhibitor LY2109761, TβRI kinase inhibitor LY580276, galunisertib LY2157299, TGF-β receptor inhibitor SB-431542, TGF-β1 receptor inhibitor SB-505124, and a combination thereof.

According to the present disclosure, the sPLA2 hydrolysable liposome may have a diameter ranging from 80 to 150 nm.

According to the present disclosure, the first HA-SH nanoparticle may have a diameter ranging from 80 to 150 nm.

According to the present disclosure, the second HA-SH nanoparticle may have a diameter ranging from 80 to 150 nm.

The present disclosure also provides a method for treating an ocular disorder in a subject, comprising administering to an eye of the subject an ocular drug delivery system described above.

According to the present disclosure, the ocular disorder may be selected from the group consisting of conjunctivitis, corneal ulcer, dry eye syndrome, infectious keratitis, uveitis, recurrent corneal erosion syndrome (RCES), and acute angle-closure glaucoma.

The disclosure will be further described by way of the following examples. However, it should be understood that the following examples are solely intended for the purpose of illustration and should not be construed as limiting the disclosure in practice.

EXAMPLES

General Procedures:
1. Statistical Analysis

In the following examples, each group was subjected to the same experiment three times. The experimental data are expressed as mean±standard error of the mean (SEM), and were analyzed using one-way analysis of variance (ANOVA) so as to assess the difference between all the groups. Statistical significance is indicated by $p<0.05$.

Example 1. Preparation of Ocular Drug Delivery System of Present Disclosure

A. Synthesis of Positively Charged Chitosan-Modified Hydrogel Film 0.82 mL of 2-hydroxyethyl methacrylate (HEMA), 0.1 mL of acrylic acid (AAc), 0.04 mL of 2,2-diethoxy acetophenone (DEAP), 0.04 mL of trimethylolpropane triacrylate (TMPTA), and 100 mg of ZnO were mixed, followed by photopolymerization using a UV Lamp (Blak-Ray 160 W) at 365 nm for 30 minutes. The hydrogel film thus obtained was immersed in 95% ethanol for 24 hours, followed by immersion in deionized water for 24 hours, so as to remove unreacted materials. Thereafter, the hydrogel film was subjected to vacuum drying for 48 hours.

0.47 g of sodium azide ($NaN_3$) was dissolved in 1.18 mL of a tetrabutylammonium bromide solution (4.9 mg/mL), followed by addition with 0.57 mL of chloromethyloxirane. The resultant mixture was placed in a dark place at room temperature and allowed to react for 12 hours. Thereafter, the aforesaid dried hydrogel film was added to the mixture, followed by reaction at room temperature in the dark for 24 hours. The azide-functionalized hydrogel film thus obtained was washed with deionized water, followed by vacuum drying for 48 hours.

0.1 mmol of N-alkylated chitosan was dissolved in 50 mL of tetrahydrofuran (THF), and sufficient mixing was conducted. The dried azide-functionalized hydrogel film was immersed in the resultant solution and then stirred (100 rpm) for 10 minutes, followed by adding 10 mL of a 1 M copper sulfate solution. To the resultant mixture was added dropwise 50 mL of a 1 M ascorbic acid solution. Subsequently, stirring was conducted for 48 hours under nitrogen. Thereafter, THF was removed under vacuum, followed by adding 10 mL of dichloromethane and 10 mL of ammonia solution. After reacting for 10 minutes, the positively charged chitosan-modified hydrogel film thus obtained was washed with deionized water, followed by vacuum drying for 48 hours. The resultant dried positively charged chitosan-modified hydrogel film was used for the following example.

B. Synthesis of Secretory Phospholipase A2 (sPLA2) Hydrolysable Liposome 5 mg of dipalmitoyl-phosphatidylcholine (DPPC) was dissolved in 1 mL of a chloroform/methanol (2:1, v/v) solution, followed by reacting at 50° C. for 3 hours. To the resultant mixture was added 5 mL of a solution (containing 5 mg of epigallocatechin gallate (EGCG), 1 mM NaCl, and 15 wt % ethanol), followed by hydration for 2 hours. Thereafter, the mixture thus obtained was subjected to ultrasonication at 20° C. for 10 minutes, so as to form sPLA2 hydrolysable liposomes which encapsulated EGCG (i.e., an anti-inflammatory drug) and had a negative surface charge.

The sPLA2 hydrolysable liposomes were observed to have an average diameter of about 100 nm using a transmission electron microscope (TEM). Furthermore, the sPLA2 hydrolysable liposomes were analyzed to have a zeta-potential of about −26.7 mV by laser Doppler microelectrophoresis using Zetasizer Nano-ZS (Malvern Instruments Ltd., Worcestershire, UK).

C. Synthesis of First Thiolated Hyaluronic Acid (HA-SH) Nanoparticle

The first thiolated hyaluronic acid (HA-SH) nanoparticles were prepared as follows.

In step (a), 200 mg of hyaluronic acid was dissolved in 80 mL of deionized water, and the solution thus prepared was sequentially added with 1 mL of a β-1,3-glucan solution (200 μg/mL) and 136 mL of acetone, followed by stirring for 15 minutes to form a glucan-containing hyaluronic acid solution.

In step (b), 40 mg of 1-ethyl-3-(3-dimethylaminopropyl) carbodiimide hydrochloride (EDC) and 20 mg of adipic acid dihydrazide (ADH) were dissolved in 2 mL of deionized water, followed by adding the glucan-containing hyaluronic acid solution obtained in step (a). After stirring for 30 minutes, to the resultant mixture was added 131 mL of acetone, followed by stirring for 3 hours, so as to form hyaluronic acid nanoparticles.

In step (c), 200 mg of the hyaluronic acid nanoparticles obtained in step (b) was mixed with 50 mL of deionized water, and the resultant mixture was adjusted to pH 5.5 through addition of a 0.1 M HCl solution, followed by adding EDC (50 mM) and N-hydroxysuccinimide (NHS)(50 mM). After stirring well at room temperature for 20 minutes, the mixture thus obtained was added with 250 mg of L-cysteine, and the pH thereof was adjusted to 6 by adding dropwise a 1 N HCl solution. After stirring at room temperature for 4 hours, first HA-SH nanoparticles were obtained. The first HA-SH nanoparticles encapsulated β-1, 3-glucan (i.e., a wound-healing drug) and had a negative surface charge and a crosslinking index of 19%.

The first HA-SH nanoparticles were observed to have an average diameter of about 20 nm using a transmission electron microscope (TEM). Furthermore, the first HA-SH nanoparticles were analyzed to have a zeta-potential of about −30.1 mV by laser Doppler microelectrophoresis using Zetasizer Nano-ZS (Malvern Instruments Ltd., Worcestershire, UK).

D. Synthesis of Second Thiolated Hyaluronic Acid (HA-SH) Nanoparticle

The second HA-SH nanoparticles were prepared generally according to the procedures described in the abovementioned section C of this example, except that: in step (a), a solution containing 20 μM SB-431542 (CAS No. 301836-41-9) was used to replace the β-1,3-glucan solution (thus, a SB-431542-containing hyaluronic acid solution was formed); and in step (b), 80 mg of EDC and 40 mg of ADH were dissolved in 2 mL of deionized water, followed by adding the SB-431542-containing hyaluronic acid solution obtained in step (a). The second HA-SH nanoparticles thus obtained encapsulated SB-431542 (i.e., a TGF-β receptor inhibitor) and had a negative surface charge and a crosslinking index of 42%.

The second HA-SH nanoparticles were observed to have an average diameter of about 20 nm using a transmission electron microscope (TEM). Furthermore, the second HA-SH nanoparticles were analyzed to have a zeta-potential of about −24.8 mV by laser Doppler microelectrophoresis using Zetasizer Nano-ZS (Malvern Instruments Ltd., Worcestershire, UK).

E. Electrostatic Attraction

The positively charged chitosan-modified hydrogel film obtained in the above section A, the sPLA2 hydrolysable liposomes obtained in the above section B, the first HA-SH nanoparticles obtained in the above section C, and the second HA-SH nanoparticles obtained in the above section D were mixed together with a balanced salt solution (BSS), such that the sPLA2 hydrolysable liposomes, the first HA-SH nanoparticles, and the second HA-SH nanoparticles were attached to the positively charged chitosan-modified hydrogel film by electrostatic attraction. The ocular drug delivery system thus obtained was used for the following example.

Example 2. Evaluation of In Vitro Drug Release Profile of Ocular Drug Delivery System In order to evaluate the drug release profiles of the sPLA2 hydrolysable liposomes, the first HA-SH nanoparticles, and the second HA-SH nanoparticles, the following analyses were conducted.

Experimental Procedures:

A suitable amount of the ocular drug delivery system obtained in Example 1 was immersed in 1 mL of a sPLA2 solution (containing 0.1 mg/mL sPLA2), followed by incubation at 37° C. with reciprocal shaking (100 rpm) in a thermostatically controlled water bath for a designated time period ranging from 0 minutes to 168 hours. Sample solutions were taken at each time point of 0, 1, 2, 3, 4, 5, 12, 24, 48, 72, 96, 120, 144, and 168 hours.

The sample solutions thus obtained were centrifuged at 1000 rpm for 3 minutes. The resultant supernatants were collected and then subjected to high performance liquid chromatography (HPLC) analysis using a L-2400 UV detector, a L-2130 pump (Hitachi, Tokyo, Japan), and a Mightysil RP-18 column (Kanto Chemical, Tokyo, Japan).

The HPLC operating conditions applied were described as follows. The mobile phase was 90% water with 0.1% trifluroacetic acid and 10% acetonitrile, and the flow rate of the mobile phase was 1 mL/min. The injection volume was 10 μL. The elution peak was detected by measuring absorbance at 280 nm (for EGCG), 305 nm (for β-1,3 glucan), and 274 nm (for SB-431542), respectively.

The amount of EGCG released from the sPLA2 hydrolysable liposomes was calculated with reference to a standard calibration curve of EGCG. Results from five independent measurements were averaged and further used to calculate the cumulative released amount of EGCG.

The release profile of β-1,3-glucan from the first HA-SH nanoparticles and the release profile of SB-431542 from the second HA-SH nanoparticles were evaluated substantially according to the procedures as described above, except that the ocular drug delivery system was immersed in 1 mL of a hyaluronidase solution (containing 100 U/mL hyaluronidase).

Figure 2:
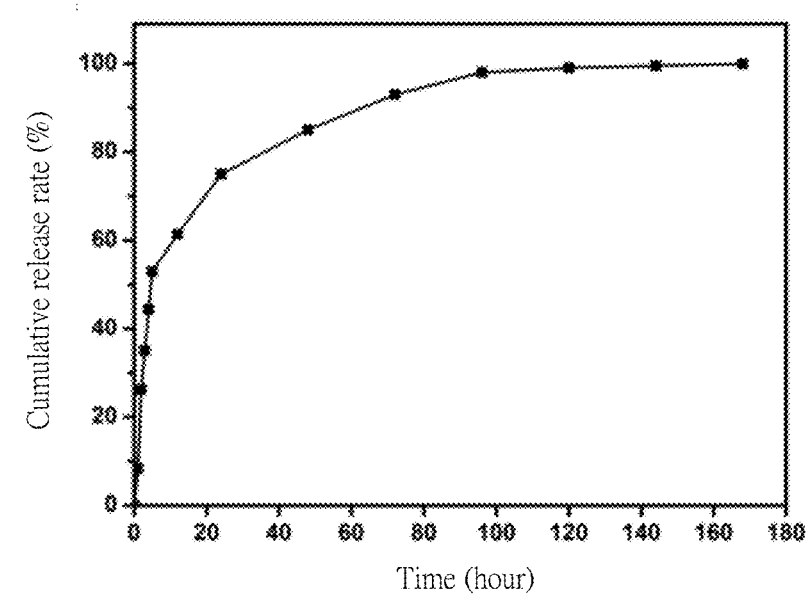
FIG. 2 shows the cumulative release profile of β-1,3-glucan.
Figure 3:
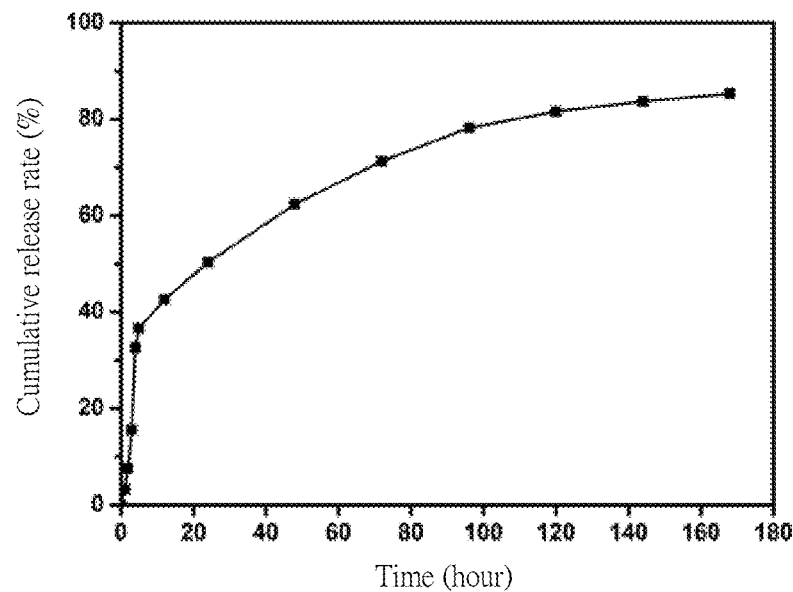
FIG. 3 shows the cumulative release profile of SB-431542.

Results:

FIGS. 1-3 respectively show the cumulative release profiles of EGCG, β-1,3-glucan, and SB-431542. As shown in FIG. 1, EGCG was released in a large amount within 8 hours following the initiation of the release test, and the cumulative release rate of EGCG from the sPLA2 hydrolysable liposomes was reached to 90% within 20 hours. As shown in FIG. 2, β-1,3 glucan was released at a release rate slower than that of EGCG, and the cumulative release rate of β-1,3 glucan from the first HA-SH nanoparticles was reached to 90% within 70 hours after the initiation of the release test. In addition, as shown in FIG. 3, SB-431542 was released at a release rate slower than those of EGCG and β-1,3 glucan, and the cumulative release rate of SB-431542 from the second HA-SH nanoparticles was reached to 80% at the 160th hour after the initiation of the release test.

These results indicate that the ocular drug delivery system of the present disclosure is capable of releasing EGCG, β-1,3-glucan, and SB-431542 in sequence at multiple stages, and can allow a sustained release of these drugs and enhance these drugs' bioavailability.

Example 3. In Vitro Test

A. Source and Cultivation of Ocular Cell (a) Rabbit corneal keratocytes (RCK) were prepared from adult male New Zealand white rabbits (National Laboratory Animal Breeding and Research Center, Taipei, Taiwan, ROC) in accordance with the procedures described in Jui-Yang Lai et al. (2012), *International Journal of Nanomedicine*, 7:1101-1114. RCK were grown in a 6-cm Petri dish containing KSFM (keratinocyte serum-free medium) supplemented with 10,000 U/mL penicillin, 10 mg/mL streptomycin, and 25 μg/mL amphotericin B. The RCK were cultivated in an incubator with culture conditions set at 37° C. and 5% $CO_2$. Medium change was performed every two days. Cell passage was performed when the cultured cells reached 80%-90% of confluence.

(b) Rabbit corneal epithelial (SIRC) cells (BCRC NO: 60093) were obtained from the Bioresources Collection and Research Center (BCRC) of Food Industry Research and Development Institute (FIRDI) (Hsinchu, Taiwan). The SIRC cells were grown in a regular growth medium containing minimum essential medium (MEM) and 10% fetal bovine serum (FBS), and were cultivated in a humidified atmosphere (5% $CO_2$, 37° C.).

B. Anti-Inflammation Test

SIRC cells were divided into 4 groups, including two control groups (i.e., a normal control group and a positive control group) and two experimental groups (i.e., experimental groups 1 and 2). Each group of the SIRC cells was incubated in a respective well of a 48-well culture plate containing 100 μL of regular growth medium containing minimum essential medium (MEM) and 10% FBS at $2\times10^4$ cells/well, followed by cultivation in an incubator (37° C., 5% $CO_2$) for 72 hours.

Thereafter, a cell culture insert (pore size: 0.4 μm) (Thermo Fisher Scientific) containing a piece of the positively charged chitosan-modified hydrogel film prepared in section A of Example 1 was placed into the well of the experimental group 1, and a cell culture insert containing a piece of the ocular drug delivery system prepared in section E of Example 1 was placed into the well of the experimental group 2. To the well of a respective one of the positive control group, the experimental group 1, and the experimental group 2 was added 100 μL of a culture medium solution (containing 1 ng/mL IL-1β), whereas the SIRC cells of the normal control group were not treated with IL-1β. All the groups were cultivated in an incubator (37° C., 5% $CO_2$) for 18 hours.

25 μL of the respective resultant cell culture was taken and was added into a well of a 96-well plate coated with a monoclonal antibody specific for human IL-6, and the resultant mixture was allowed to stand still at 4° C. for 24 hours. After washing with a wash buffer (Cat. No. WA126, R&D Systems), a biotin-labeled anti-human cytokine antibody was added into each well, and the resultant mixture was allowed to stand still at room temperature for 1 hour. Thereafter, 200 μL of human IL-6 conjugate (Cat. No. 890046, R&D Systems) was added and allowed to react at room temperature for 30 minutes. The level of IL-6 in each group was detected using the Luminex 200™ system (Luminex Co., Austin, Ill.). The data were analyzed using the StatLIA® software (Brendan Technologies Inc., Carlsbad, Calif.).

Figure 4:
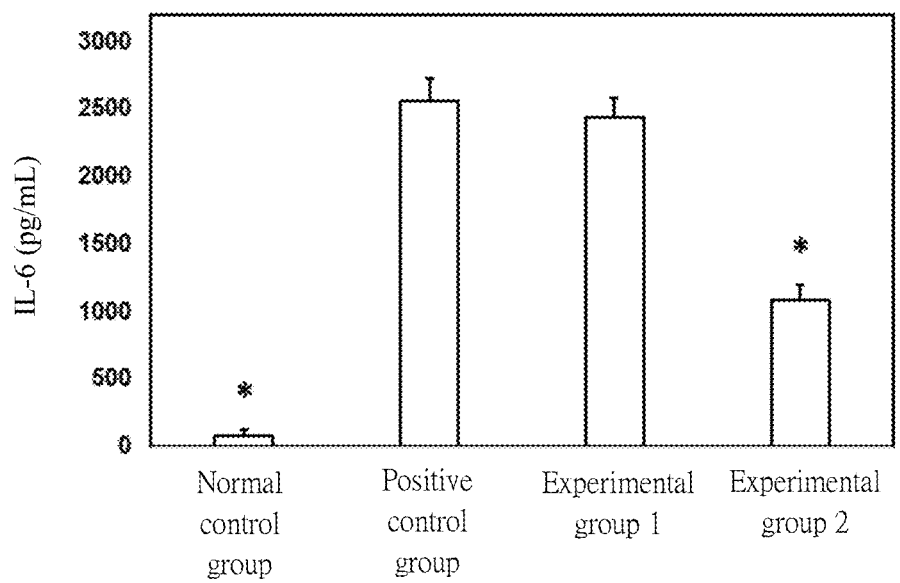
FIG. 4 shows the level of IL-6 in SIRC (statens seruminstitut rabbit cornea) cells of each group of Example 3, infra, in which the symbol "*" represents statistically significant differences ($p<0.05$) when compared with the positive control group.

FIG. 4 shows the level of IL-6 in the SIRC cells of each group. It can be seen from FIG. 4 that the IL-6 level of the positive control group was significantly higher than that of the normal control group, indicating that IL-1β can induce inflammation in SIRC cells.

In addition, the IL-6 level of the experimental group 2 was significantly lower than that of the experimental group 1. These results indicate that the ocular drug delivery system of the present disclosure can effectively release EGCG from the sPLA2 hydrolysable liposomes under an inflammatory state, and hence is capable of reducing inflammation.

C. Cell Migration Assay

A cell culture insert was placed into each well of a 12-well culture plate. The SIRC cells were seeded into the culture tanks on both sides of the culture insert at a cell number of $1\times10^4$ cells and then incubated overnight to allow cell attachment. Thereafter, the culture insert was removed to create a cell-free gap with a width of about 180 μm, and then the liquid in each well was removed. Each well was washed three times with phosphate-buffered saline (PBS), followed by addition of 200 μL of Eagle's minimum essential medium (MEM).

The SIRC cells were divided into 4 groups, including two control groups (i.e., a normal control group and a positive control group) and two experimental groups (i.e., experimental groups 1 and 2). Into the well of the positive control group, 200 μL of a β-1,3-glucan solution (containing 200 μg/mL β-1,3-glucan) was added. Into the well of the experimental group 1, a piece of the positively charged chitosan-modified hydrogel film prepared in section A of Example 1 was added. Into the well of the experimental group 2, a piece of the ocular drug delivery system prepared in section E of Example 1 was added. The SIRC cells in the normal control group received no treatment. All the groups were cultivated in an incubator (37° C., 5% $CO_2$) for 18 hours.

At 0 and 18 hours after incubation, the cell migration profile of the SIRC cells in each group was photographed using an inverted phase contrast microscope (Nikon, Melville, N.Y., USA), and the width of the cell-free gap was measured by ImageJ software. The cell migration rate (%) was calculated using the following Equation (I):

$$\text{Cell migration rate (\%)} = [A-B]/A \times 100 \quad (I)$$

Wherein

A=the width of the cell-free gap at 0 hour (i.e., the initial width of the cell-free gap); and B=the width of the cell-free gap at 18 hours.

Figure 5:
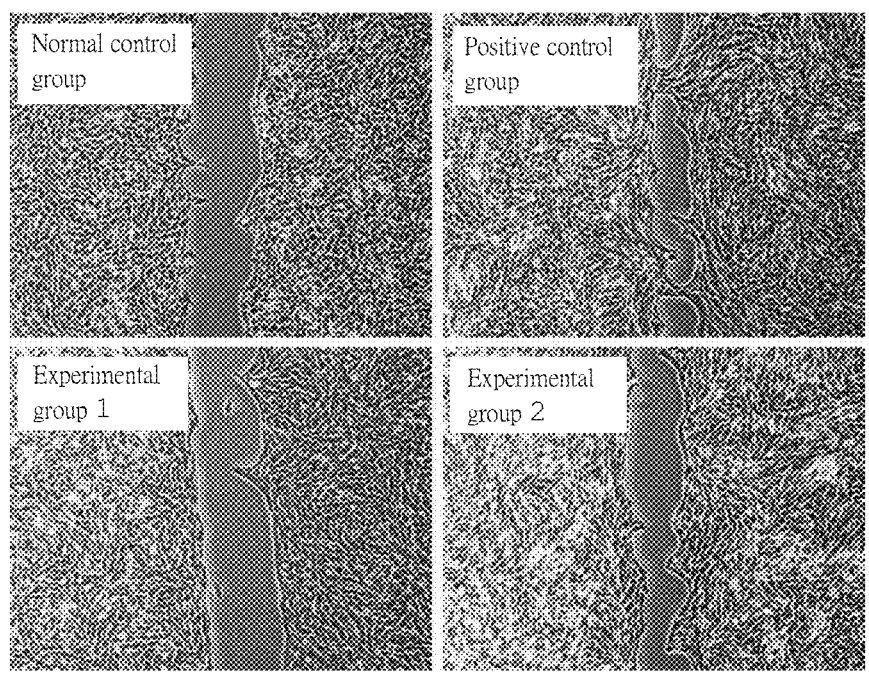
FIG. 5 shows the cell migration profile of SIRC cells in each group of Example 3, infra.

FIG. 5 shows the cell migration profile of the SIRC cells in each group, and Table 1 shows the cell migration rate of the SIRC cells in each group. It can be seen from FIG. 5 and Table 1 that the cell migration of the SIRC cells in the positive control group was significantly improved, and the cell migration rate of the positive control group was higher than those of the other groups, indicating that β-1,3-glucan can enhance corneal epithelial cell migration.

In addition, the cell migration rate of the experimental group 2 was higher than those of the normal control group and the experimental group 1. These results indicate that the ocular drug delivery system of the present disclosure can effectively release β-1,3-glucan from the first HA-SH nanoparticles in the presence of hyaluronidase, and hence is capable of healing wounds by promoting corneal epithelial cell migration.

TABLE 1

| Group | Cell migration rate (%) |
|---|---|
| Normal control group | 9 |
| Positive control group | 73 |
| Experimental group 1 | 17 |
| Experimental group 2 | 65 |

D. Keratocan Expression of RCK

RCK were divided into 5 groups, including three control groups (i.e., a normal control group, a positive control group, and a negative control group) and two experimental groups (i.e., experimental groups 1 and 2). Each group of RCK was incubated in a respective well of a 48-well culture plate containing 100 μL of KSFM at $2\times10^4$ cells/well, followed by cultivation in an incubator (37° C., 5% $CO_2$) for 24 hours.

Thereafter, into the well of the negative control group, 100 μL of a TGF-β solution (containing 10 ng/mL TGF-β) was added. Into the well of the positive control group, 100 μL of a TGF-β solution (containing 10 ng/mL TGF-β) and 20 μM TGF-β receptor inhibitor SB-431542 were added.

Into the well of the experimental group 1, 100 μL of a TGF-β solution (containing 10 ng/mL TGF-β) and a piece of the positively charged chitosan-modified hydrogel film prepared in section A of Example 1 were added. Into the well of the experimental group 2, 100 μL of a TGF-β solution (containing 10 ng/mL TGF-β), 100 μL of a hyaluronidase solution (containing 100 U/mL hyaluronidase), and a piece of the ocular drug delivery system prepared in section E of Example 1 were added. The RCK in the normal control group received no treatment. All the groups were cultivated in an incubator (37° C., 5% $CO_2$) for 48 hours.

The keratocan expression of the cultured cells was detected at messenger RNA (mRNA) levels. Briefly, total RNA was isolated from the cultured cells with TRIzol reagent according to the manufacturer's procedure. The resultant total RNA of each group was proceeded to a reverse transcription performed under the reaction conditions shown in Table 2.

TABLE 2

| Content | Volume (μL) |
| --- | --- |
| RNA (10 μg) | 10 |
| dNTPs (25 mM) (Promega, Madison, WI, USA) | 8 |
| 5X buffer (Promega, Madison, WI, USA) | 40 |
| RNasin (40 units/μL) | 10 |
| M-MLV reverse transcriptase (9.5 units/μL) (Promega, Madison, WI, USA) | 10 |
| Dithiothreitol (DTT) (0.1M) (Promega, Madison, WI, USA) | 20 |
| Water | 100 |

Operation conditions: Denaturation was conducted at 94° C. for 1 minute; and then denaturation was conducted at 57° C. for 60 seconds; primer annealing and elongation was conducted at 72° C. for 120 seconds; a total of thirty five cycles were conducted.

A primer pair having the following nucleotide sequence was used in detecting the gene expression of human keratocan gene (KERA).

Forward Primer
5'-ctcacgtggctttgatgtgt-3' (SEQ ID NO:1)
Reverse Primer
5'-gacctttgtgaggcgattgt-3' (SEQ ID NO:2)

Quantitative real-time reverse transcription polymerase chain reaction (RT-PCR) was performed on a Light-Cycler instrument (Roche Diagnostics, Indianapolis, Ind., USA) according to the manufacturer's instructions with FastStart DNA Master SYBR Green I reagent (Roche Diagnostics). The mRNA expression of keratocan was normalized with that of glyceraldehyde 3-phosphate dehydrogenase (GAPDH). The experiment was performed in triplicate, and the results are expressed as relative keratocan mRNA level (%) as compared to the control group (i.e., the cells cultured with culture medium only).

Figure 6:
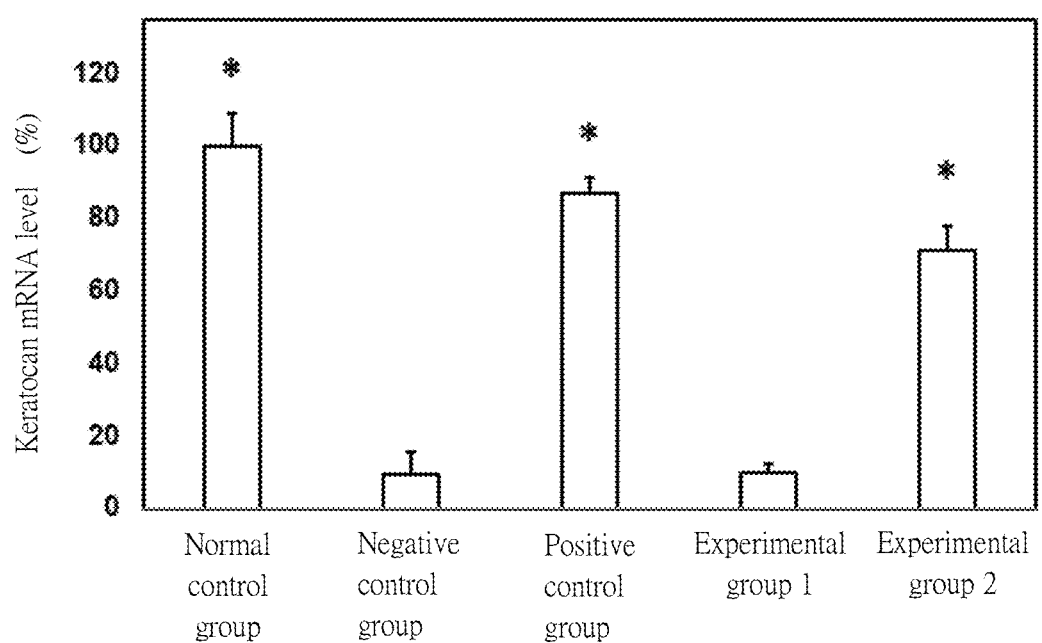
FIG. 6 shows the keratocan mRNA level of rabbit corneal keratocytes in each group of Example 3, infra, in which the symbol "*" represents statistically significant differences ($p<0.05$) when compared with the negative control group.

FIG. 6 shows the keratocan mRNA level of the RCK in each group. It can be seen from FIG. 6 that the keratocan mRNA level of the negative control group was significantly lower than that of the normal control group, indicating that TGF-β1 can differentiate RCK into myofibroblasts with prominent focal adhesions, causing RCK to lose their normal phenotype.

In addition, the keratocan mRNA level of the experimental group 2 was higher than those of the negative control group and the experimental group 1. These results indicate that the ocular drug delivery system of the present disclosure can effectively release SB-431542 from the second HA-SH nanoparticles in the presence of hyaluronidase, thereby suppressing TGF-β signaling and maintaining keratocan-expressing keratocyte phenotype. Therefore, the applicant infers that the ocular drug delivery system of the present disclosure is capable of reducing scar formation during ocular surface reconstruction.

Example 4. Animal Model Test

A. Experimental Materials:
(1) Test Animals

New Zealand white rabbits (16-20 weeks old, a body weight of 3-3.5 Kg) were purchased from National Laboratory Animal Breeding and Research Center (Taipei, Taiwan, ROC). The rabbits were kept in an animal room with an independent air conditioning system under the following laboratory conditions: a 12 hour light/12 hour dark cycle, a temperature of 21-24° C., and a relative humidity of 45-75%. Furthermore, water and feed were provided ad libitum for all experimental animals. All animal testing procedures were approved by the Institutional Review Board and were carried out in accordance with the ARVO Statement for the Use of Animals in Ophthalmic and Vision Research.

(2) Comparative Gel

A piece of the positively charged chitosan-modified hydrogel film prepared in section A of Example 1 was immersed in 1 mL of a drug solution (containing 1 mg/mL EGCG, 200 μg/mL β-1,3-glucan, and 20 μM SB-431542) for 24 hours. The resultant gel was used as a comparative gel.

(3) Anaesthetic Drugs

Zoletil® was purchased from Virbac Co., Ltd. (Carros, France), Rompun® was purchased from Bayer Pharmaceutical Co., Ltd., and a 0.5% proparacaine hydrochloride ophthalmic solution was purchased from Virbac Co., Ltd. (Carros, France).

B. Experimental Procedures:

New Zealand white rabbits were divided into 5 groups, including three control groups (i.e., a normal control group, a positive control group, and a negative control group) and two experimental groups (i.e., experimental groups 1 and 2) (n=6 for each group). The cornea of each rabbit in the positive control group, the negative control group, the experimental group 1, and the experimental group 2 was treated with 50 μL of a 0.2% benzalkonium chloride (BAC) solution two times a day for a total period of 7 days, so as to induce corneal epithelial damage. The rabbits in the normal control group received no treatment.

Thereafter, for the positive control group, the cornea of each rabbit was treated with 50 μL of an antibiotic eye drop. For the experimental group 1, the cornea of each rabbit was treated with a piece of the comparative gel obtained in the above Item (2). For the experimental group 2, the cornea of each rabbit was treated with a piece of the ocular drug delivery system prepared in section E of Example 1. The cornea of each rabbit in the normal control group and the negative control group received no treatment.

After the 7-day treatment described above, Zoletil® (dose in use: 2.5 mg/Kg) and Rompun® (dose in use: 1 mg/Kg) were intramuscularly injected into the rabbits of each group. Furthermore, for each group, 2 drops of 0.5% proparacaine hydrochloride were administered onto the eye surface of the rabbits. Thereafter, 2 μL of fluorescein sodium (1%, w/v) was topically instilled into the conjunctival sac of the rabbits. At 2 hours and 7 days after instilling the fluorescein sodium, the corneal morphology of the rabbit eye was observed by slit-lamp biomicroscopy (Topcon Optical, Tokyo, Japan).

C. Results:

FIG. 7 shows the slit-lamp biomicroscopic images of rabbit eyes at 2 hours and 7 days after instilling fluorescein sodium. It can be seen from FIG. 7 that in the normal control group, the cornea was clear and no corneal scar was observed, while in the negative control group, the cornea was filled with fluorescein sodium and corneal scars were observed, indicating that BAC can induce ocular surface inflammation, which results in the corneal epithelial cells lacking the ability to migrate, causing the fluorescence in the eye unable to be diminished at 7 days after the fluorescein sodium instillation. Besides, similar results were observed with respect to the positive control group and the experimental group 1, indicating that the topical administration of the eye drop or the comparative gel did not exhibit therapeutic effect.

In contrast, the corneal scar area and the residual fluorescein sodium of the experimental group 2 were significantly lower than those of the negative control group, the positive control group, and the experimental group 1 at 7 days after the fluorescein sodium instillation. These results indicate that the ocular drug delivery system of the present disclosure can effectively release EGCG, β-1,3-glucan, and SB-431542 in sequence at multiple stages, and hence is capable of reducing inflammation, healing wounds by promoting corneal epithelial cell migration, and reducing scar formation during ocular surface reconstruction.

All patents and references cited in this specification are incorporated herein in their entirety as reference. Where there is conflict, the descriptions in this case, including the definitions, shall prevail.

While the disclosure has been described in connection with what are considered the exemplary embodiments, it is understood that this disclosure is not limited to the disclosed embodiments but is intended to cover various arrangements included within the spirit and scope of the broadest interpretation so as to encompass all such modifications and equivalent arrangements.

SEQUENCE LISTING

<110> CHANG GUNG UNIVERSITY

<120> OCULAR DRUG DELIVERY SYSTEM AND USES THEREOF

<130> PE-61709-AM

<160> 2

<170> PatentIn version 3.5

<210> 1

<211> 20

<212> DNA

<213> Artificial Sequence

<220>

<223> Forward primer of keratocan gene for quantitative real-time RT-PCR

<400> 1
ctcacgtggc tttgatgtgt 20

<210> 2

<211> 20

<212> DNA

<213> Artificial Sequence

<220>

<223> Reverse primer of keratocan gene for quantitative real-time RT-PCR

<400> 2
gacctttgtg aggcgattgt

---

SEQUENCE LISTING

```
<160> NUMBER OF SEQ ID NOS: 2

<210> SEQ ID NO 1
<211> LENGTH: 20
<212> TYPE: DNA
<213> ORGANISM: Artificial Sequence
<220> FEATURE:
<223> OTHER INFORMATION: Forward primer of keratocan gene for
      quantitative real-time PCR

<400> SEQUENCE: 1
ctcacgtggc tttgatgtgt                                                   20

<210> SEQ ID NO 2
<211> LENGTH: 20
<212> TYPE: DNA
<213> ORGANISM: Artificial Sequence
<220> FEATURE:
<223> OTHER INFORMATION: Reverse primer of keratocan gene for
      quantitative real-time PCR

<400> SEQUENCE: 2
gacctttgtg aggcgattgt                                                   20
```

---

What is claimed is:

1. An ocular drug delivery system, comprising:
a positively charged chitosan-modified hydrogel which is obtained by a process including subjecting a hydrogel to a click chemistry reaction with a chitosan;

a secretory phospholipase A2 (sPLA2) hydrolysable liposome encapsulating an anti-inflammatory drug and having a negative surface charge;

a first thiolated hyaluronic acid (HA-SH) nanoparticle encapsulating a wound-healing drug and having a negative surface charge; and a second HA-SH nanoparticle encapsulating a transforming growth factor-β (TGF-β) inhibitor and having a negative surface charge, the second HA-SH nanoparticle having a crosslinking index higher than that of the first HA-SH nanoparticle;

wherein the sPLA2 hydrolysable liposome, the first HA-SH nanoparticle, and the second HA-SH nanoparticle are attached to the positively charged chitosan-modified hydrogel by electrostatic attraction.

2. The ocular drug delivery system according to claim 1, wherein the click chemistry reaction is performed using a chemical agent selected from the group consisting of azidated epichlorohydrin, sodium azide, sodium nitrite, triflyl azide, imidazole-1-sulfonyl azide hydrochloride, and a combination thereof.

3. The ocular drug delivery system according to claim 2, wherein the chemical agent is sodium azide.

4. The ocular drug delivery system according to claim 1, wherein the positively charged chitosan-modified hydrogel has a UV-blocking material selected from the group consisting of $ZnO$, $TiO_2$, $CeO_2$, and a combination thereof.

5. The ocular drug delivery system according to claim 1, wherein the sPLA2 hydrolysable liposome has a phospholipid selected from the group consisting of dipalmitoyl-phosphatidylcholine (DPPC), anionic dipalmitoyl-phosphatidylglycerol (DPPG), and a combination thereof.

6. The ocular drug delivery system according to claim 5, wherein the phospholipid is dipalmitoyl-phosphatidylcholine.

7. The ocular drug delivery system according to claim 1, wherein the anti-inflammatory drug is selected from the group consisting of a phenolic drug, a flavonoid drug, an antibiotic, a steroid drug, a non-steroidal anti-inflammatory drug, and a combination thereof.

8. The ocular drug delivery system according to claim 7, wherein the phenolic drug is selected from the group consisting of epigallocatechin gallate (EGCG), p-coumaric acid, ferulic acid, gallic acid, gentisic acid, 4-hydroxybenzoic acid, protocatechuic acid, sinapinic acid, syringic acid, and vanillic acid, and a combination thereof.

9. The ocular drug delivery system according to claim 7, wherein the flavonoid drug is selected from the group consisting of (+)-catechin, (+)-gallocatechin, (−)-epicatechin (EC), (−)-epigallocatechin (EGC), and a combination thereof.

10. The ocular drug delivery system according to claim 7, wherein the antibiotic is selected from the group consisting of tobramycin, besifloxacin, ciprofloxacin, levofloxacin, ofloxacin, levofloxacin, moxifloxacin, and a combination thereof.

11. The ocular drug delivery system according to claim 7, wherein the steroid drug is selected from the group consisting of dexamethasone, hypromellose, betamethasone sodium phosphate, prednisolone acetate, prednisolone sodium, and a combination thereof.

12. The ocular drug delivery system according to claim 7, wherein the non-steroidal anti-inflammatory drug is selected from the group consisting of ketorolac, bromfenac, diclofenac, flurbiprofen, nepafenac, phenylephrine, and a combination thereof.

13. The ocular drug delivery system according to claim 1, wherein the wound-healing drug is selected from the group consisting of β-1,3-glucan, human growth hormone (HGH), insulin-like growth factor 1 (IGF-1), insulin, testosterone, and a combination thereof.

14. The ocular drug delivery system according to claim 1, wherein the TGF-β inhibitor is selected from the group consisting of trabedersen, TGF-β receptor type I antisense oligonucleotide AP-11014, lerdelimumab, metelimumab, fresolimumab GC-1008, D10 monoclonal antibody, TGF-β receptor type 1/type II inhibitor LY2109761, TβRI kinase inhibitor LY580276, galunisertib LY2157299, TGF-β receptor inhibitor SB-431542, TGF-β1 receptor inhibitor SB-505124, and a combination thereof.

15. The ocular drug delivery system according to claim 1, wherein the sPLA2 hydrolysable liposome has a diameter ranging from 80 to 150 nm.

16. The ocular drug delivery system according to claim 1, wherein the first HA-SH nanoparticle has a diameter ranging from 80 to 150 nm.

17. The ocular drug delivery system according to claim 1, wherein the second HA-SH nanoparticle has a diameter ranging from 80 to 150 nm.

18. A method for treating an ocular disorder in a subject, comprising administering to an eye of the subject an ocular drug delivery system of claim 1.

19. The method according to claim 18, wherein the ocular disorder is selected from the group consisting of conjunctivitis, corneal ulcer, dry eye syndrome, infectious keratitis, uveitis, recurrent corneal erosion syndrome (RCES), and acute angle-closure glaucoma.

* * * * *